United States Patent [19]

Rello

[11] Patent Number: 5,255,684
[45] Date of Patent: Oct. 26, 1993

[54] ULTRASONIC PROBE ASSEMBLY
[75] Inventor: Michael J. Rello, Harleysville, Pa.
[73] Assignee: Interspec, Inc., Ambler, Pa.
[21] Appl. No.: 782,678
[22] Filed: Oct. 25, 1991
[51] Int. Cl.⁵ .............................................. A61B 8/00
[52] U.S. Cl. ........................... 128/662.06; 128/660.1
[58] Field of Search .................... 128/660.09, 662.06, 128/660.1, 620; 73/633

[56] References Cited

U.S. PATENT DOCUMENTS

| | | |
|---|---|---|
| 4,014,207 | 3/1977 | Meyer et al. . |
| 4,149,419 | 4/1979 | Connell, Jr. et al. . |
| 4,269,066 | 5/1981 | Fischer . |
| 4,272,991 | 6/1981 | Cribbs . |
| 4,330,874 | 5/1982 | Sorwick . |
| 4,362,058 | 12/1982 | Abele . |
| 4,374,525 | 2/1983 | Baba . |
| 4,375,818 | 3/1983 | Suwaki et al. . |
| 4,385,521 | 5/1983 | Hagen et al. . |
| 4,494,548 | 1/1985 | Buon et al. . |
| 4,543,960 | 10/1985 | Harui et al. ................ 128/662.06 |
| 4,567,895 | 2/1986 | Putzke . |
| 4,637,256 | 1/1987 | Sugiyama et al. . |
| 4,732,156 | 3/1988 | Nakamura . |
| 4,756,313 | 7/1988 | Terwilliger . |
| 4,757,818 | 7/1988 | Angelsen . |
| 4,787,247 | 11/1988 | Wuchinich et al. . |
| 4,807,634 | 2/1989 | Enjoji et al. .................. 128/660.01 |
| 4,841,979 | 6/1989 | Dow et al. . |
| 4,850,362 | 7/1989 | Rello et al. . |
| 4,913,158 | 4/1990 | Kikuchi et al. . |
| 5,048,529 | 9/1991 | Blumenthal .................... 128/660.1 |
| 5,050,610 | 9/1991 | Oaks et al. .................... 128/662.06 |
| 5,090,414 | 2/1992 | Takano ...................... 128/662.06 |
| 5,181,514 | 1/1993 | Solomon et al. ........... 128/662.06 X |

FOREIGN PATENT DOCUMENTS 0079525 5/1983 European Pat. Off. .
0317049 5/1989 European Pat. Off. .

Primary Examiner—Francis Jaworski
Attorney, Agent, or Firm—Ratner & Prestia

[57] ABSTRACT

An ultrasonic probe assembly in which an ultrasonic transducer is mechanically scanned in response to a drive motor which is located in a housing spaced from the transducer such that the transducer can be positioned in a body cavity of patient while the housing containing the drive motor remains outside the body of the patient.

15 Claims, 5 Drawing Sheets

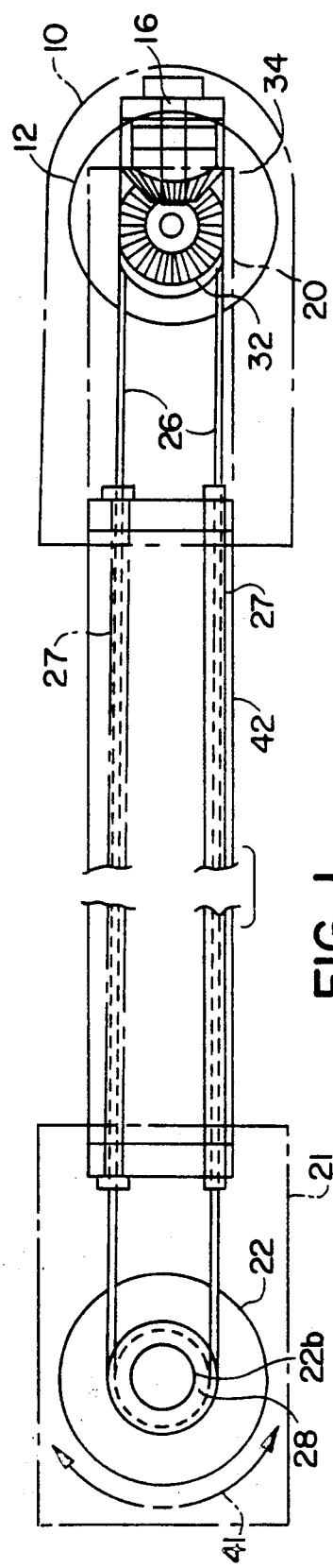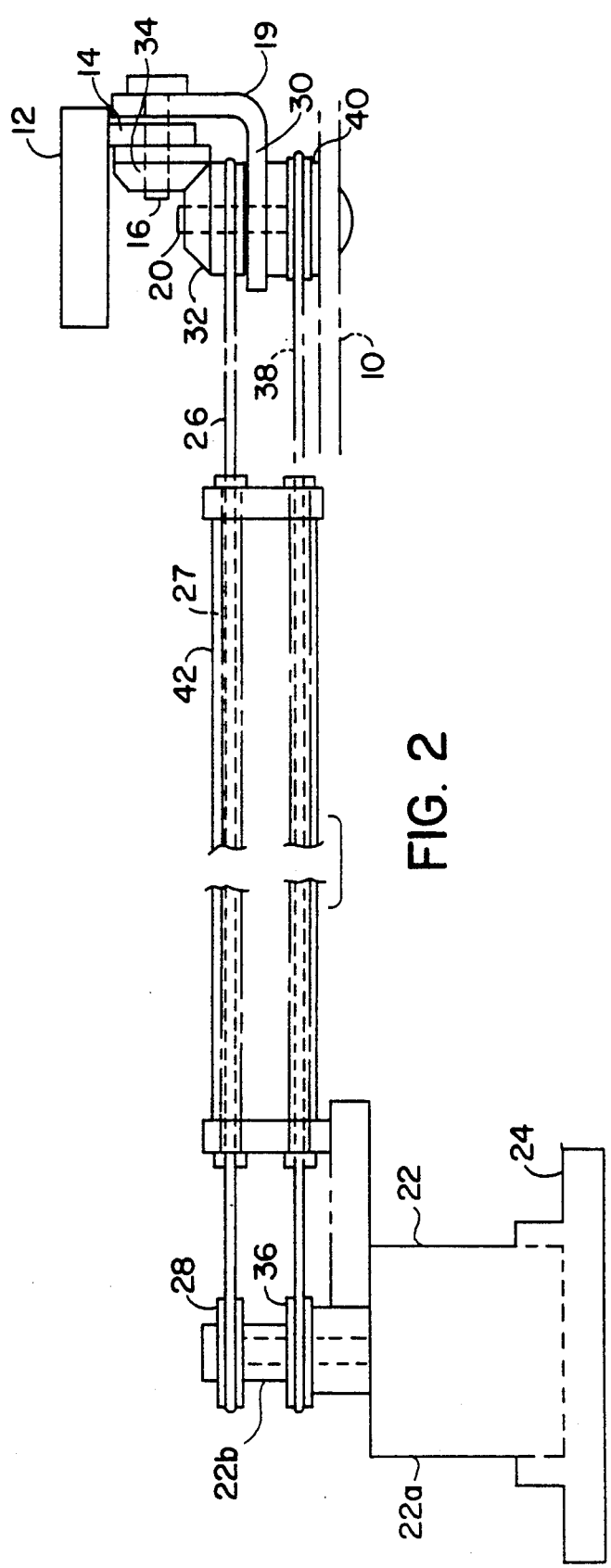

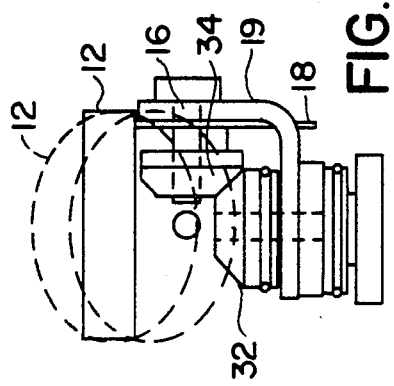
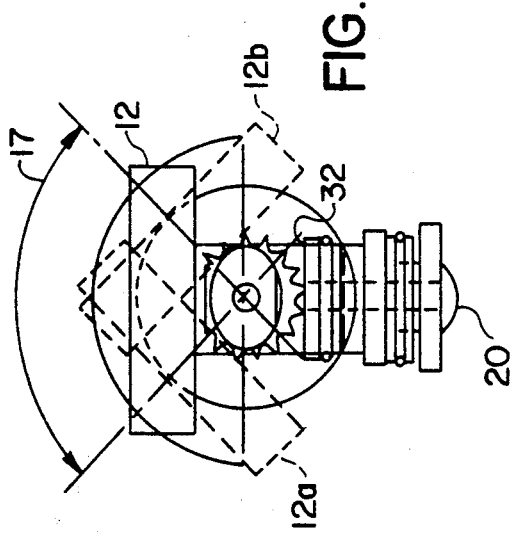
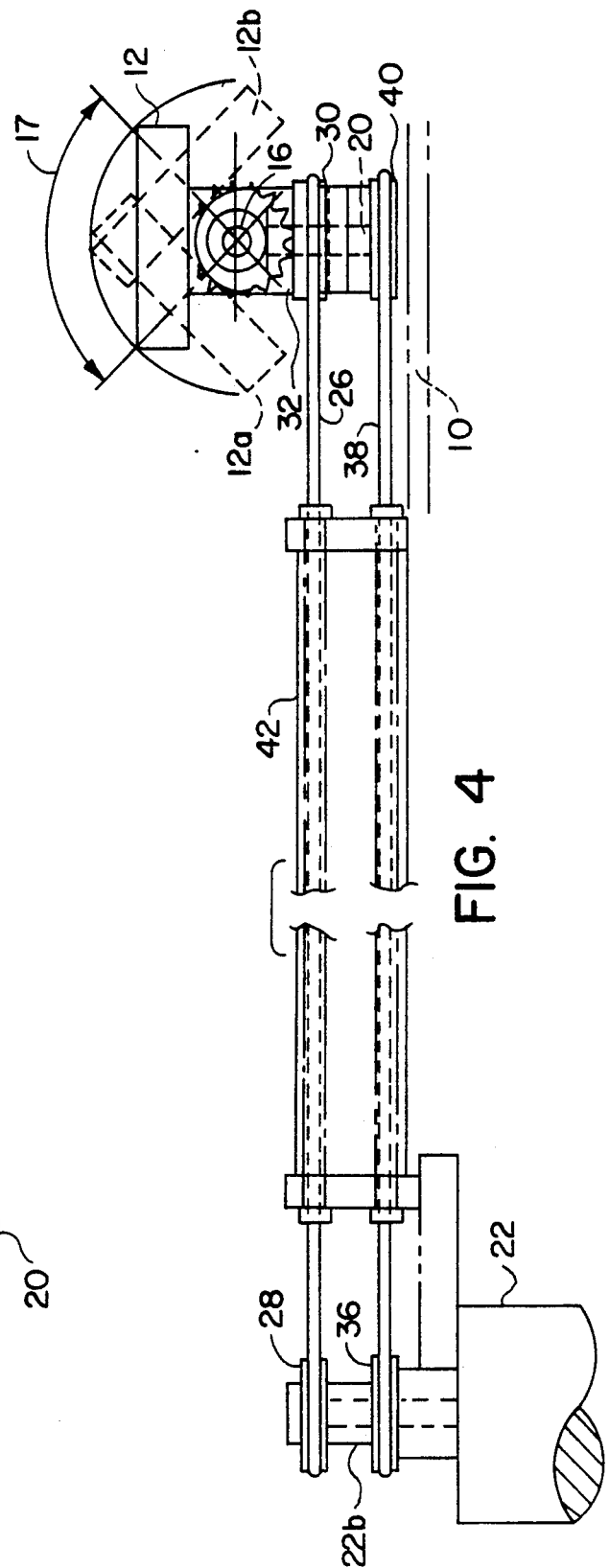

ULTRASONIC PROBE ASSEMBLY

TECHNICAL FIELD

The present invention relates, in general, to ultrasonic imaging and, in particular, to an ultrasonic probe assembly with the ultrasonic transducer arranged for insertion into a body cavity.

BACKGROUND OF THE INVENTION

Ultrasonic probe assemblies having the ultrasonic transducer arranged for insertion into a body cavity (i.e. prostate probes, esophageal probes, vaginal probes) are in widespread use. Typically, the ultrasonic transducer, the transducer mount mechanism and the motor which imparts scanning movement to the ultrasonic transducer are housed at one end of an endoscope. Power to the motor and electrical signals, from which the image is developed, are conducted along wires extending through the endoscope. In addition, for those ultrasonic probe assemblies arranged for multi-plane scanning, the cables by which the scan plane of the ultrasonic transducer is changed mechanically extend through the endoscope to the transducer mount mechanism from a control remote from the transducer mount mechanism.

It is apparent that the sizes of the ultrasonic transducer, the transducer mount mechanism and the scanning motor dictate the size of the housing inserted into the body cavity. Often, the size of this housing is too large for the desired applications of the ultrasonic probe assembly.

SUMMARY OF THE INVENTION

An ultrasonic probe assembly, constructed in accordance with the present invention, includes a first housing, a ultrasonic transducer and mounting means for mounting the ultrasonic transducer to the first housing for scanning movement of the ultrasonic transducer. Also included in this ultrasonic probe assembly are a second housing spaced from the first housing, a drive motor mounted in the second housing and having an output driver, and coupling means, including flexible connecting means, extending between the output driver of the motor and the ultrasonic transducer for imparting scanning movement to the ultrasonic transducer in response to the output driver. The flexible connecting means have a length which permits positioning the first housing with the ultrasonic transducer within a body cavity of a patient while the second housing remains outside the body of the patient.

When the present invention is incorporated in a multi-plane imaging ultrasonic probe assembly, the assembly also includes second mounting means for mounting the first mounting means and the ultrasonic transducer to the first housing for pivotal movement of the first mounting means about an axis perpendicular to the axis about which the ultrasonic transducer is scanned. Also included are selection means attached to the second housing containing the drive motor for setting a selected pivotal position of the first mounting means and second coupling means, including second flexible connecting means, extending between the selection means and the second mounting means for positioning the first mounting means in response to the selection means. The second flexible connecting means have a length substantially coextensive with the first flexible connecting means.

BRIEF DESCRIPTION OF THE DRAWINGS

FIG. 1 is a top view of one preferred embodiment of an ultrasonic probe assembly constructed in accordance with the present invention.

FIG. 2 is a side view of the FIG. 1 ultrasonic probe assembly.

FIG. 3 is an end view of the FIGS. 1 and 2 ultrasonic probe assembly.

FIG. 4 is a side view of the FIGS. 1 and 2 ultrasonic probe assembly with the ultrasonic transducer positioned to scan in a plane different from its scan plane in FIGS. 1 and 2.

FIG. 5 is an end view of the FIGS. 1 and 2 ultrasonic probe assembly with the ultrasonic transducer positioned to scan as illustrated in FIG. 4.

DETAILED DESCRIPTION OF THE INVENTION

Figure 6:
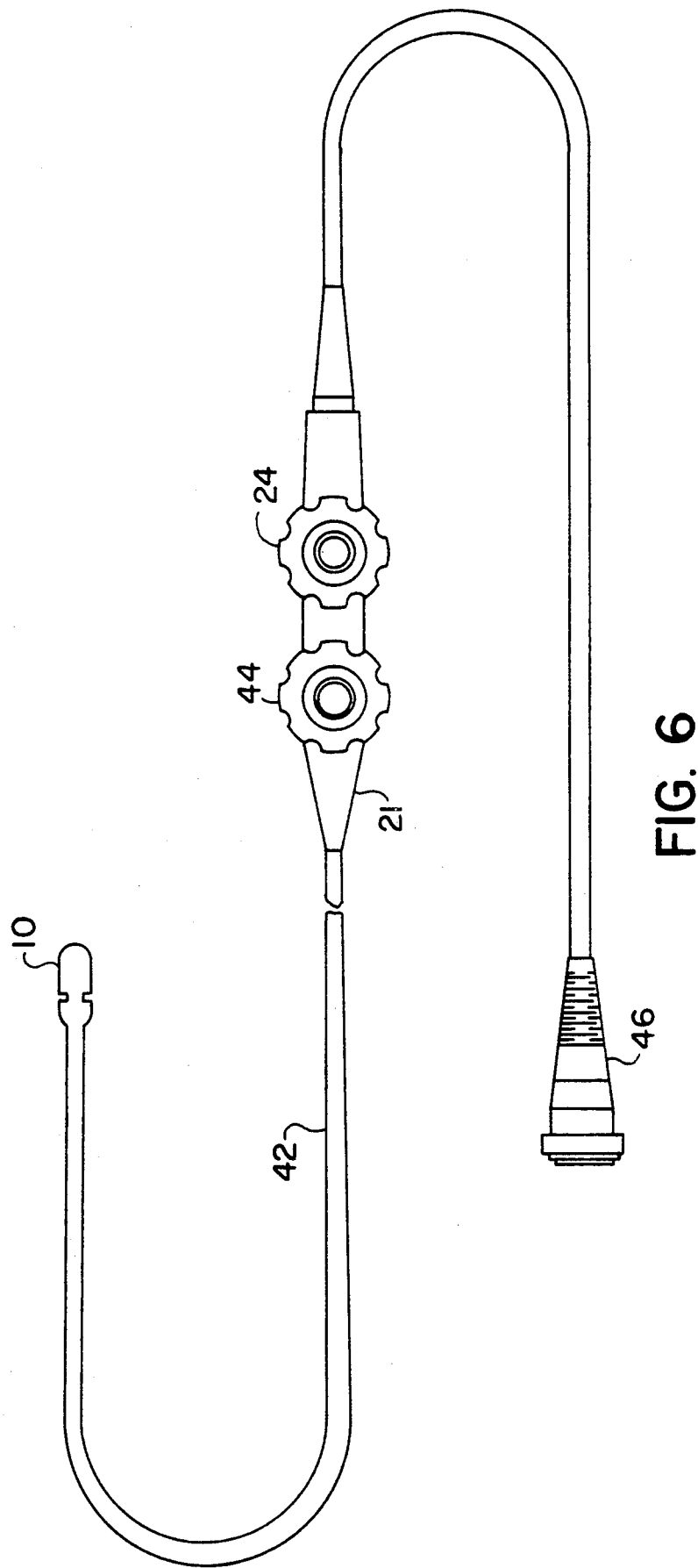
FIG. 6 is a plan view of an endoscope in which the ultrasonic probe assembly of FIGS. 1 through 5 can be incorporated.

Referring to FIGS. 1 through 5, an ultrasonic probe assembly, constructed in accordance with the present invention, includes a first housing 10, a ultrasonic transducer 12 and first mounting means for mounting transducer 12 for scanning movement of transducer 12 about a first axis. Ultrasonic transducer 12 can be of conventional construction and operation such as a 3.5-5 MHz transducer supplied by Echo Ultrasound and used typically for cardiac imaging. Ultrasonic transducer 12 is attached to a leg 14 and is mounted, for the embodiment of the present invention being described, by a pivot shaft 16 on which leg 14 is mounted and which defines an axis for scanning movement of ultrasonic transducer 12. FIG. 3 shows by dashed lines 12a and 12b the range of oscillatory scanning motion of ultrasonic transducer 12. A double-ended arrow 17 defines this range of motion which typically is 100 degrees.

The first mounting means and ultrasonic transducer 12 are mounted to housing 10 for pivotal movement of the first mounting means about a second axis which is perpendicular to the scan axis of transducer 12. This is accomplished by second mounting means which, for the embodiment of the present invention being described, include a bracket 19 and a pivot shaft 20. By this arrangement the plane of scanning of ultrasonic transducer 12 can be changed so that the body part, such as the heart, which is being imaged can be viewed in different ways (i.e. in longitudinal and transverse sections or any section in between). FIGS. 4 and 5 show ultrasonic transducer 12 positioned to scan in a plane different from the scan plane position of ultrasonic transducer 12 in FIGS. 1, 2 and 3.

An ultrasonic probe assembly, constructed in accordance with the present invention, also includes a second housing 21 spaced from first housing 10 and a drive motor 22 mounted in housing 21 and having a motor housing 22a and an output driver shaft 22b. Drive motor 22, which can be a DC reciprocating motor, provides the drive for oscillatory scanning movement of ultrasonic transducer 12. Drive motor 22 is rotatably mounted in housing 21, so that it can pivot when the scan plane of ultrasonic transducer 12 is to be changed.

Attached to motor housing 22a are selection means, in the form of a knob 24, for setting a selected pivotal position of the first mounting means in housing 10. The position of knob 24 and, therefore, the position of motor 22 determine the scan plane of ultrasonic transducer 12.

An ultrasonic probe assembly, constructed in accordance with the present invention, further includes first coupling means extending between output driver shaft 22b of motor 22 and ultrasonic transducer 12 for imparting scanning movement to transducer 12 in response to oscillatory movement of output driver shaft 22b. The first coupling means include, for the embodiment of the present invention being described, a flexible connection 26, made up of two lengths, attached at a first end to a drive pulley 28 which is fixed to output driver shaft 22b of motor 22. Flexible connection 26 also is attached at a second end to a pulley 30 which is mounted on pivot shaft 20 for reciprocating movement. Each length of flexible connection 26 extends through a sleeve 27 the opposite ends of which are anchored in housings 10 and 21. Integral with pulley 30 is a first bevel gear 32 which meshes with a second bevel gear 34 to which leg 14 is attached. As a result, the oscillatory drive provided by motor 22 is imparted to ultrasonic transducer 12 through drive pulley 28, flexible connection 26, pulley 30, bevel gears 32 and 34, and leg 14. The length of flexible connection 26 and the length of each sleeve permits positioning first housing 10 and ultrasonic transducer 12 within a body cavity of a patient while second housing 21 with motor 22 remains outside the body of the patient.

An ultrasonic probe assembly, constructed in accordance with the present invention, further includes second coupling means extending between the scan-plane selection means at housing 21 and the second mounting means at housing 10 for positioning the first mounting means at housing 10 in response to movement of the selection means. The second coupling means include, for the embodiment of the present invention being described, a pulley 36 fixed to motor housing 22a and a second flexible connection 38 fixed at one end to pulley 36 and at a second end to a pulley 40 which is integral with bracket 19. As a result, as knob 24 is turned, as represented by the double-ended arrow 41, this movement is imparted to bracket 19 through motor housing 22a, pulley 36, flexible connection 38 and pulley 40 to change the scan plane of ultrasonic transducer 12. The range of scan-plane variation can be up to one hundred eighty degrees. The length of flexible connection 38 is substantially coextensive with flexible connection 26, so that knob 24 with housing 21 is outside the body of the patient while housing 10 and ultrasonic transducer 12 are within a body cavity of the patient.

Preferably, flexible connections 26 and 38 extend through a flexible tube 42, the ends of which are attached by suitable means to housings 10 and 21. In addition, wires (not shown) which power ultrasonic transducer 12 and conduct imaging signals from transducer 12 extend through flexible tube 42.

FIG. 6 illustrates the ultrasonic probe assembly of FIGS. 1 through 5 incorporated in an endoscope. Housings 10 and 21 are connected by flexible tube 42 through which flexible connections 26 and 38 extend. Knob 24 on housing 21 functions, as previously described, to change the scan plane of the ultrasonic transducer in housing 10. The drive motor (not shown in FIG. 6) is located in housing 21. A second knob 44 on housing 21 controls bending of the end of the flexible endoscope upward, downward and sideways to permit the end of the endoscope to make turns as it is passed through the body to the body cavity at which imaging is to take place. The wires (not shown) which power the ultrasonic transducer (not shown in FIG. 6) and conduct imaging signals from the transducer extend to a connector 46 which is adapted for connection into suitable signal processing and imaging equipment.

Figure 7A:
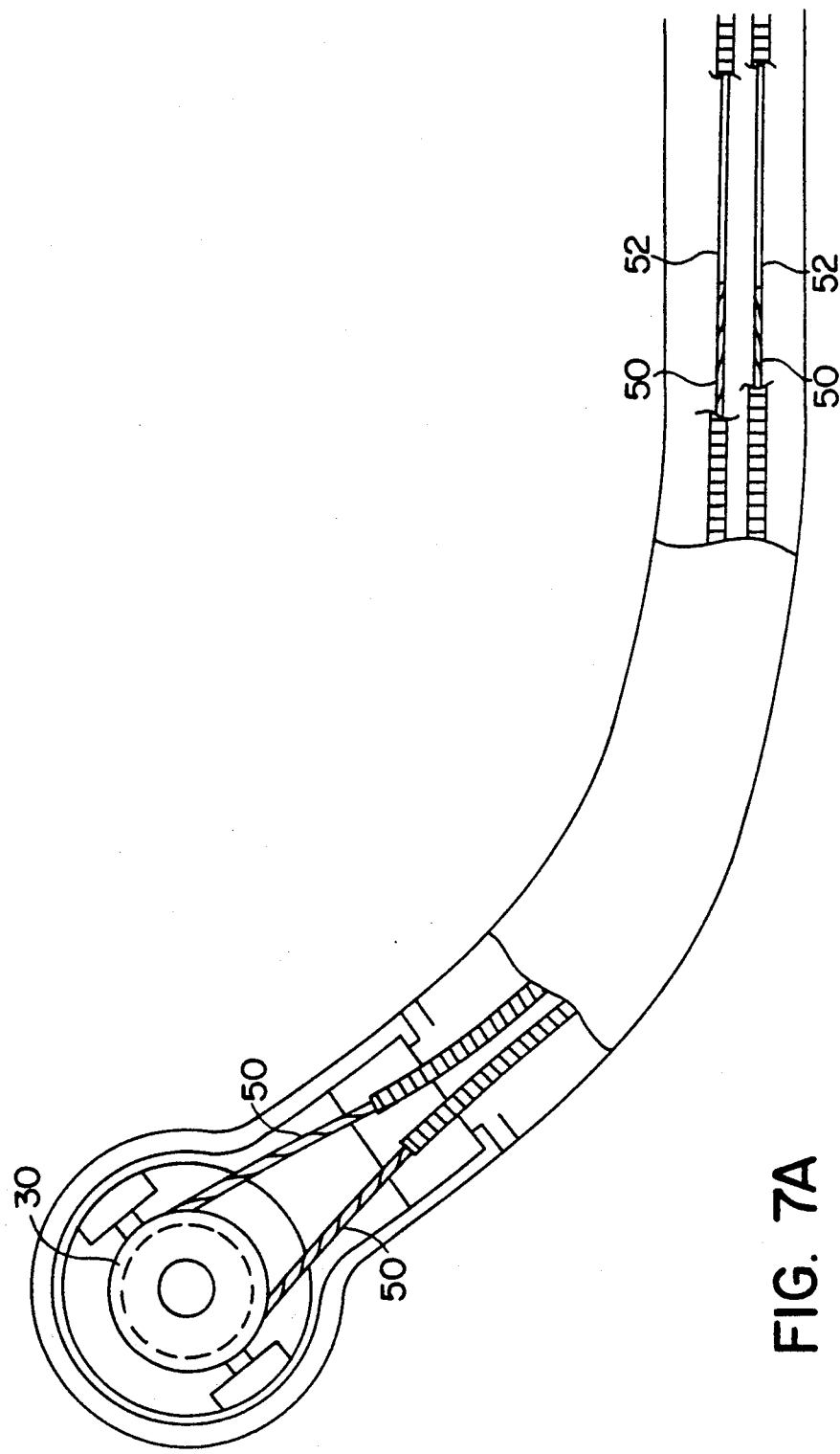
FIGS. 7A and 7B are sectional views which illustrate in more detail and on a larger scale the flexible connections between the two housings of the ultrasonic probe assembly of FIGS. 1 through 5 incorporated in the endoscope of FIG. 6.
Figure 7B:
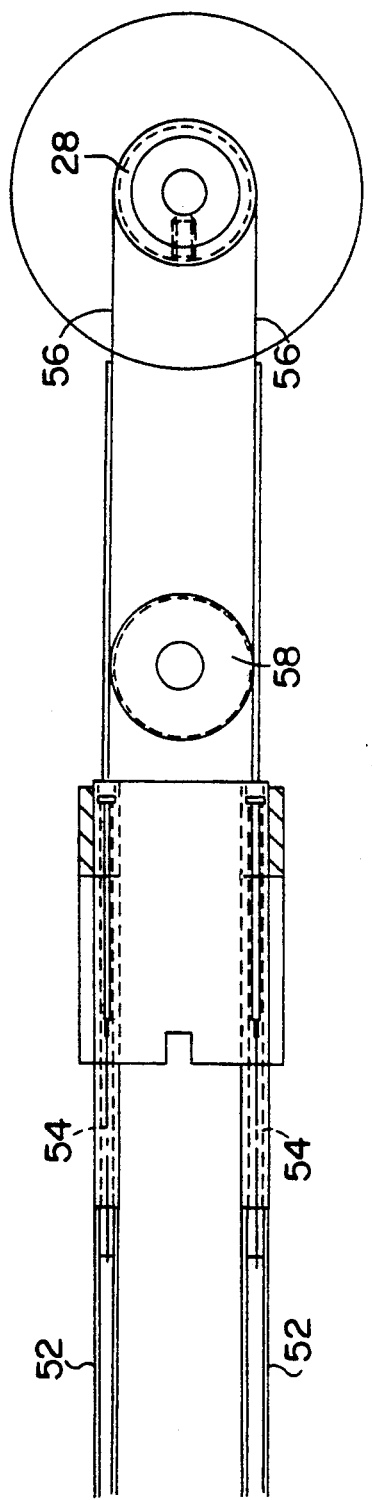

Referring to FIGS. 7A and 7B, which should be viewed with the right-hand end of FIG. 7A leading to the left-hand end of FIG. 7B, flexible connection 26 from the FIGS. 1 through 5 ultrasonic probe assembly can include a multi-strand steel cable section 50 which is pinned to pulley 30. As the two lengths of multi-strand steel cable section 50 to either side of pulley 30 are pulled or pushed in response to the reciprocating movement of output driver shaft 22b of motor 22, pulley 30 turns.

Flexible connection 26 also includes a single-strand steel music wire section 52 which is butt-welded to multi-strand steel cable section 50. At its opposite end, single-strand steel music wire section 52 is soldered to a steel surgical tubing section 54.

Steel surgical tubing section 54 is soldered to an endless belt 56 which extends between pulley 28 and an idler pulley 58. With endless belt 56 pinned to pulley 28 and pulley 28 fixed to output driver shaft 22b of motor 22, as output driver shaft 22b reciprocates, pulley 28 is driven and also reciprocates to cause endless belt 56 to undergo movements in opposite directions.

The arrangement of flexible connection 26 which has just been described results in a connection having reduced hysteresis and backlash. Multi-strand steel cable section 50 is sufficiently flexible to conform to the tight radii in housing 10. Single-strand steel music wire section 52 provides sufficient stiffness and rigidity so that it can be pushed in push/pull operation. Steel surgical tubing section 54 serves as the inside wiper for the seal at the transition from wet to dry in an endoscope. Endless belt 56, in conjunction with idler pulley 58, besides converting the rotary motion of output driver shaft 22b of motor 22 to linear motion, adds stiffness and rigidity to effect push/pull motion.

Flexible connection 38, by which the scan plane of ultrasonic transducer 12 is changed, can be arranged similar to flexible connection 26 just described.

The foregoing has set forth an exemplary and preferred embodiment of the present invention. It will be understood, however, that various other alternative embodiments will occur to those of ordinary skill in the art without departure from the spirit and scope of the present invention.

What is claimed is:

1. An ultrasonic probe assembly comprising:
a first housing;
an ultrasonic transducer;
first mounting means for mounting said ultrasonic transducer for scanning movement of said transducer in a selected scan plane about a first axis;
second mounting means for mounting said first mounting means and sail ultrasonic transducer to said first housing for pivotal movement of said first mounting means with respect to said first housing about a second axis which is perpendicular to said first axis;
a second housing spaced from said first housing;

a drive motor rotatably mounted in said second housing and having a motor housing and an output driver;

selection means attached to said motor housing for setting a selected pivotal position of said first mounting means corresponding to said selected scan plane;

first coupling means, including first flexible connecting means, extending between said output driver of said drive motor and said ultrasonic transducer for imparting scanning movement to said transducer in response to movement of said output driver, said first flexible connecting means having a length which permits positioning said first housing and said transducer within a body cavity of a patient while said second housing remains outside the body of the patent;

and second coupling means, including second flexible connecting means, extending between said selection means and said second mounting means for positioning said first mounting means in response to movement of said selection means, said second flexible connecting means having a length substantially coextensive with said first flexible connecting means.

2. An ultrasonic probe assembly according to claim 1 wherein said drive motor is a reciprocating motor and said scanning movement of said ultrasonic transducer is oscillatory.

3. An ultrasonic probe assembly according to claim 2 further including a flexible tube extending between said first housing and said second housing and through which said first flexible connecting means and said second flexible connecting means extend.

4. A ultrasonic probe assembly according to claim 2 wherein the range of scanning movement of said ultrasonic transducer is 100 degrees.

5. An ultrasonic probe assembly according to claim 4 wherein the range of scan-plane variation of said ultrasonic transducer is one hundred eighty degrees.

6. An endoscope comprising:

a first housing;

an ultrasonic transducer for developing signals representative of a body part being imaged;

first mounting means for mounting said ultrasonic transducer for scanning movement of said transducer in a selected scan plane about a first axis;

second mounting means for mounting said first mounting means and said ultrasonic transducer to said first housing for pivotal movement of said first mounting means with respect to said first housing about a second axis which is perpendicular to said first axis;

a second housing spaced from said first housing;

a drive motor rotatably mounted in said second housing and having a motor housing and an output driver;

selection means attached to said motor housing for setting a selected pivotal position of said first mounting means corresponding to said selected scan plane;

first coupling means, including first flexible connecting means, extending between said output driver of said drive motor and said ultrasonic transducer for imparting scanning movement to said transducer in response to movement of said output driver, said first flexible connecting means having a length which permits positioning said first housing and said transducer within a body cavity of a patient to image a body part while said second housing remains outside the body of the patient;

second coupling means, including second flexible connecting means, extending between said selection means and said second mounting means for positioning said first mounting means in response to movement of said selection means, said second flexible connecting means having a length substantially coextensive with said first flexible connection means;

a flexible tube extending between said first housing and said second housing and through which said first flexible connecting means and said second flexible connecting means extend;

and means for conducting said signals developed by said ultrasonic transducer to signal processing and imaging equipment.

7. An ultrasonic probe assembly comprising:

a first housing;

an ultrasonic transducer;

mounting means for mounting said ultrasonic transducer to said first housing for scanning movement of said transducer;

a second housing spaced from said first housing;

a drive motor rotatably mounted in said second housing and having an output driver;

and coupling means, including flexible connecting means, extending between said output driver of said drive motor and said ultrasonic transducer for imparting scanning movement to said transducer in response to movement of said output driver, said flexible connecting means:

(a) including:
  (i) a multi-strand steel cable section coupled to said ultrasonic transducer,
  (ii) a single-strand steel music wire section attached to said multi-strand steel cable section,
  (iii) a steel surgical tubing section attached to said single-strand steel music wire section,
  (iv) an idler pulley, and
  (v) an endless belt to which said steel surgical tubing section is attached and which extends between said idler pulley and said output driver of said driver motor, and (b) having a length which permits positioning said first housing and said transducer within a body cavity of a patient while said second housing remains outside the body of the patient.

8. A ultrasonic probe assembly according to claim 7 wherein said coupling means further include:

(a) a first pulley in said second housing fixed to said output driver of said drive motor and to which a first end of said flexible connecting means is attached, (b) a second pulley in said first housing and to which a second end of said flexible connecting means is attached, (c) a first bevel gear in said first housing and integral with said second pulley, and (d) a second bevel gear in said first housing, meshing with said first bevel gear and connected to said ultrasonic transducer.

9. An ultrasonic probe assembly according to claim 7 wherein said coupling means further include:

(a) a first pulley in said second housing fixed to said output driver of said drive motor and to which said endless belt is attached, (b) a second pulley in said first housing and to which said multi-strand steel cable section is attached, (c) a first bevel gear in said first housing and integral with said second pulley, and (d) a second bevel gear in said first housing, meshing with said first bevel gear and connected to said ultrasonic transducer.

10. An ultrasonic probe assembly comprising:

a first housing;

an ultrasonic transducer;

first mounting means for mounting said ultrasonic transducer for oscillatory scanning movement of said transducer about a first axis;

second mounting means for mounting said first mounting means and said ultrasonic transducer to said first housing for pivotal movement of said first mounting means about a second axis which is perpendicular to said first axis;

a second housing spaced from said first housing;

a reciprocating drive motor rotatably mounted in said second housing and having a motor housing and an output driver;

selection means attached to said motor housing for setting a selected pivotal position of said first mounting means;

first coupling means, including first flexible connecting means, extending between said output driver of said drive motor and said ultrasonic transducer for imparting scanning movement to said transducer in response to movement of said output driver, said first flexible connecting means having a length which permits positioning said first housing and said transducer within a body cavity of a patient while said second housing remains outside the body of the patient and including:

(1) a first multi-strand steel cable section coupled to said ultrasonic transducer, (2) a first single-strand steel music wire section attached to said multi-strand steel cable section, (3) a first steel surgical tubing section attached to said single-strand steel music wire section, (4) a first idler pulley, and (5) a first endless belt to which said first steel surgical tubing section is attached and which extends between said first idler pulley and said output driver of said driver motor;

and second coupling means, including second flexible connecting means, extending between said selection means and said second mounting means for positioning said first mounting means in response to movement of said selection means, said second flexible connecting means having a length substantially coextensive with said first flexible connecting means and including:

(1) a second multi-strand steel cable section coupled to said second mounting means, (2) a second single-strand steel music wire section attached to said second multi-strand steel cable section, (3) a second steel surgical tubing section attached to said second single-strand steel music wire section, (4) a second idler pulley, and (5) a second endless belt to which said second steel surgical tubing section is attached and which extends between said idler pulley and said selection means.

11. An ultrasonic probe assembly according to claim 10 wherein:

(a) said first coupling means include:

(1) a first pulley in said second housing fixed to said output driver of said drive motor and to which said first endless belt is attached, (2) a second pulley in said first housing and to which said first multi-strand steel cable section is attached, (3) a first bevel gear in said first housing and integral with said second pulley, and (4) a second bevel gear in said first housing, meshing with said first bevel gear and connected to said ultrasonic transducer, and (b) said second coupling means include:

(1) a third pulley in said second housing fixed to said selection means and to which said second endless belt is attached, and (2) a fourth pulley in said first housing attached to said second mounting means and to which said second multi-strand steel cable section is attached.

12. An ultrasonic probe assembly according to claim 11 wherein said selection means include a rotatable knob fixed to said housing of said drive motor.

13. An ultrasonic probe assembly comprising:

a first housing;

an ultrasonic transducer;

first mounting means for mounting said ultrasonic transducer for oscillatory scanning movement of said transducer about a first axis;

second mounting means for mounting said first mounting means and said ultrasonic transducer to said first housing for pivotal movement of said first mounting means about a second axis which is perpendicular to said first axis;

a second housing spaced from said first housing;

a reciprocating drive motor rotatably mounted in said second housing and having a motor housing and an output driver;

a selection means attached to said motor housing for setting a selected pivotal position of said first mounting means;

first coupling means, including:

(1) first flexible connecting means, extending between said output driver of said drive motor and said ultrasonic transducer for imparting scanning movement to said transducer in response to movement of said output driver, said first flexible connecting means having a length which permits positioning said first housing and said transducer within a body cavity of a patient while said second housing remains outside the body of the patient, (2) a first pulley in said second housing fixed to said output driver of said drive motor and to which a first end of said flexible connecting means is attached, (3) a second pulley in said first housing and to which a second end of said flexible connecting means is attached, (4) a first bevel gear in said first housing and integral with said second pulley, and (5) a second bevel gear in said first housing, meshing with said first bevel gear and connected to said ultrasonic transducer;

a second coupling means, including:

(1) second flexible connecting means, extending between said selection means and said second mounting means for positioning said first mounting means in response to movement of said selection means, said second flexible connecting means having a length substantially coextensive with said first flexible connecting means, (2) a third pulley in said second housing fixed to said selection means and to which a first end of said second flexible connecting means is attached, and (3) a fourth pulley in said first housing attached to said second mounting means and to which a second end of said second flexible connecting means is attached.

14. An ultrasonic probe assembly comprising:

a first housing;

an ultrasonic transducer;

first mounting means for mounting said ultrasonic transducer for scanning movement of said transducer about a first axis;

second mounting means for mounting said first mounting means and said ultrasonic transducer to said first housing for pivotal movement of said first mounting means about a second axis which is perpendicular to said first axis;

a second housing spaced from said first housing;

a drive motor rotatably mounted in said second housing and having a motor and an output driver;

selection means attached to said motor housing for setting a selected pivotal position of said first mounting means;

first coupling means, including first flexible connecting means, extending between said output driver of said drive motor and said ultrasonic transducer for imparting scanning movement to said transducer in response to movement of said output driver, said first flexible connecting means having a length which permits positioning said first housing and said transducer within a body cavity of a patient while said second housing remains outside the body of the patient and including:

(1) first and second flexible connection lengths coupling said output driver of said motor to said transducer, and (2) first and second sleeves through which said first and said second flexible connection lengths of said first flexible connecting means, respectively, extend and having a length substantially coextensive with said first and said second flexible connection lengths of said first flexible connecting means;

and second coupling means, including second flexible connecting means, extending between said selection means and said second mounting means for positioning said first mounting means in response to movement of said selection means, said second flexible connecting means having a length substantially coextensive with said first flexible connecting means and including:

(1) first and second flexible connection lengths coupling said selection means to said second mounting means, and (2) first and second sleeves through which said first and said second flexible connection lengths of said second flexible connecting means, respectively, extend and having a length substantially coextensive with said first and said second flexible connection lengths of said second flexible connecting means.

15. An ultrasonic probe assembly according to claim 14 wherein opposite ends of said first and said second sleeves of said first flexible connecting means and opposite ends of said first and said second sleeves of said second flexible connecting means are anchored in said first and said second housings.

* * * * *

UNITED STATES PATENT AND TRADEMARK OFFICE
CERTIFICATE OF CORRECTION

PATENT NO.  : 5,255,684
DATED       : October 26, 1993
INVENTOR(S) : Michael J. Rello It is certified that error appears in the above-indentified patent and that said Letters Patent is hereby corrected as shown below:

Column 4, line 63, delete "sail" and substitute therefor --said--

Column 8, line 42, delete "a"

Column 8, line 68, delete "a" and substitute therefor --and--.

Signed and Sealed this

Thirty-first Day of May, 1994

Attest:

BRUCE LEHMAN

Attesting Officer     Commissioner of Patents and Trademarks